United States Patent [19]

Valle et al.

[11] Patent Number: 5,792,858

[45] Date of Patent: Aug. 11, 1998

[54] LYSOSPHINGOLIPID DERIVATIVES

[75] Inventors: Francesco Della Valle, Padua; Aurelio Romeo, Rome, both of Italy

[73] Assignee: FIDIA S.p.A., Abano Terme, Italy

[21] Appl. No.: 628,344

[22] Filed: Apr. 5, 1996

Related U.S. Application Data

[63] Continuation of Ser. No. 916,257, Jul. 21, 1992, Pat. No. 5,519,007, which is a continuation of Ser. No. 443,495, Nov. 30, 1989, abandoned.

[30] Foreign Application Priority Data

Dec. 2, 1988 [IT] Italy .................... 48619A/88

[51] Int. Cl.$^6$ .................... C07H 11/00; C07H 15/04; A61K 31/70; C07F 9/02
[52] U.S. Cl. .................... 536/120; 536/17.9; 536/124; 514/23; 514/53; 514/114; 514/564; 558/169; 558/175; 562/564
[58] Field of Search .................... 514/23, 53, 114, 514/564; 562/564; 558/169, 175; 536/124, 17.9, 120

[56] References Cited

U.S. PATENT DOCUMENTS

| | | |
|---|---|---|
| 4,816,450 | 3/1989 | Bell et al. |
| 4,937,232 | 6/1990 | Bell et al. |
| 4,937,328 | 6/1990 | Schmidt et al. ............ 536/18.6 |
| 4,952,683 | 8/1990 | Tschannen et al. ............ 536/18.6 |

FOREIGN PATENT DOCUMENTS

| | | |
|---|---|---|
| 0072286 | 2/1983 | European Pat. Off. |
| 0097059 | 12/1983 | European Pat. Off. |
| 62-207247 | 9/1987 | Japan |

OTHER PUBLICATIONS

M.A. Findeis et al., J. Organic Chemistry, 52, 2838–2848 (1987).

M. Kiso et al., Carbohydrate Research, 158, 101–111 (1986).

A.E. Gal et al., Chemistry and Physics of Lipids, 42, 199–207 (1986).

F. Vaccarino et al., Proc. Natl. Acad. Sci. USA, 84, 8706–8711 (1987).

Y.A. Hannun et al., J. Biol. Chemistry, 261, No. 27, 12604–12609 (1986).

A.H. Merill, Jr. et al., J. Biol. Chem., 261, No. 27, 12610–12615 (1986).

E. Wilson et al., J. Biol. Chem., 261, No. 27, 12616–12623 (1986).

(List continued on next page.)

*Primary Examiner*—John Kight
*Assistant Examiner*—Everett White
*Attorney, Agent, or Firm*—Birch, Stewart, Kolasch & Birch, LLP

[57] ABSTRACT

Novel derivatives of lysophingolipids free from sialic acids which are N-acyllysosphingolipids having one of the two formulae:

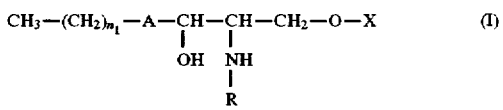

(I)

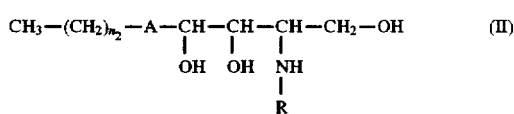

(II)

in which -A- stands for the group —CH=CH— or —CH$_2$—CH$_2$—, $n_1$ is a whole number of between 6 and 18, $n_2$ is a whole number of between 11 and 15, X is a hydrogen atom or the residue of a monosaccharide or a disaccharide or phosphorylcholine and R represents an alkyl radical derived from a saturated or unsaturated aliphatic carboxylic acid having from 2 to 24 carbon atoms substituted by one or more polar groups. The lysosphingolipid derivatives of the invention exhibit an inhibiting action on protein-kinase C activation and, thus, can be utilized in therapies for various pathologies of the nervous system.

29 Claims, 1 Drawing Sheet

OTHER PUBLICATIONS

Y.A. Hannun et al., Science, 235, 670–673.

V. Gallo et al., Proc. Natl. Acad. Sci. USA, 79, 7919–7923 (1982).

F.M. Vaccarino et al., J. Neuroscience, 7, No. 1, 65–76 (1987).

T. Yoshino et al., Biochemistry, 21, 928–934 (1982).

D. Shapiro et al., J. Organic Chemistry, 28, 2157–2160 (1963).

B. Weiss et al., J. Organic Chemistry, 35, No. 10, 3543–3546 (1970).

R.C. Arora et al., Archives of Biochem. and Biophysics, 156, 77–83 (1973).

G.A. Grabowski et al., Analytical Biochemistry, 141, 276–279 (1984).

K.R. Warren et al., J. Neurochemistry, 26, 1063–1072 (1976).

R.A. Pagano et al., Biochemistry, 27, 4439–4445 (1988).

D. Shapiro et al., J. Am. Chemical Society, 86, No. 20, 4472–4476 (1964).

B. Weiss et al., J. Chem. & Eng. Data, 13, No. 3, 450–41 (1986).

R.J. Turel et al., CA 94:83548z (Dept. of Chemistry, Univ. Bombay, India) issued 16 Mar. 1981.

I. Pascher, Chemistry and Physics of Lipids, vol. 12, 303–315 (1974).

H. Sugimoto et al., CA 112:56573n (Shionogi & Co., Ltd.) issued 12 Feb. 1990.

J.B. Hay et al., Chem. Phys. Lipids, 3, 59–69 (1969).

T. Umemura et al., Agric. Biol. Chem., 51, No. 7, 1973–1982 (1987).

H. Manev et al., J. Pharmacol. Exp. Ther., 252, No. 1, 419–427 (1990).

Lipartit et al., Neuro Report, 3, 919–921 (1992).

Seren et al., J. Pharm. & Exper. Therapeutics, 268, No. 1, 460–465 (1994).

Maney et al., Am. Soc. Pharm & Exper. Ther., 252, No. 1, 419–427 (1989).

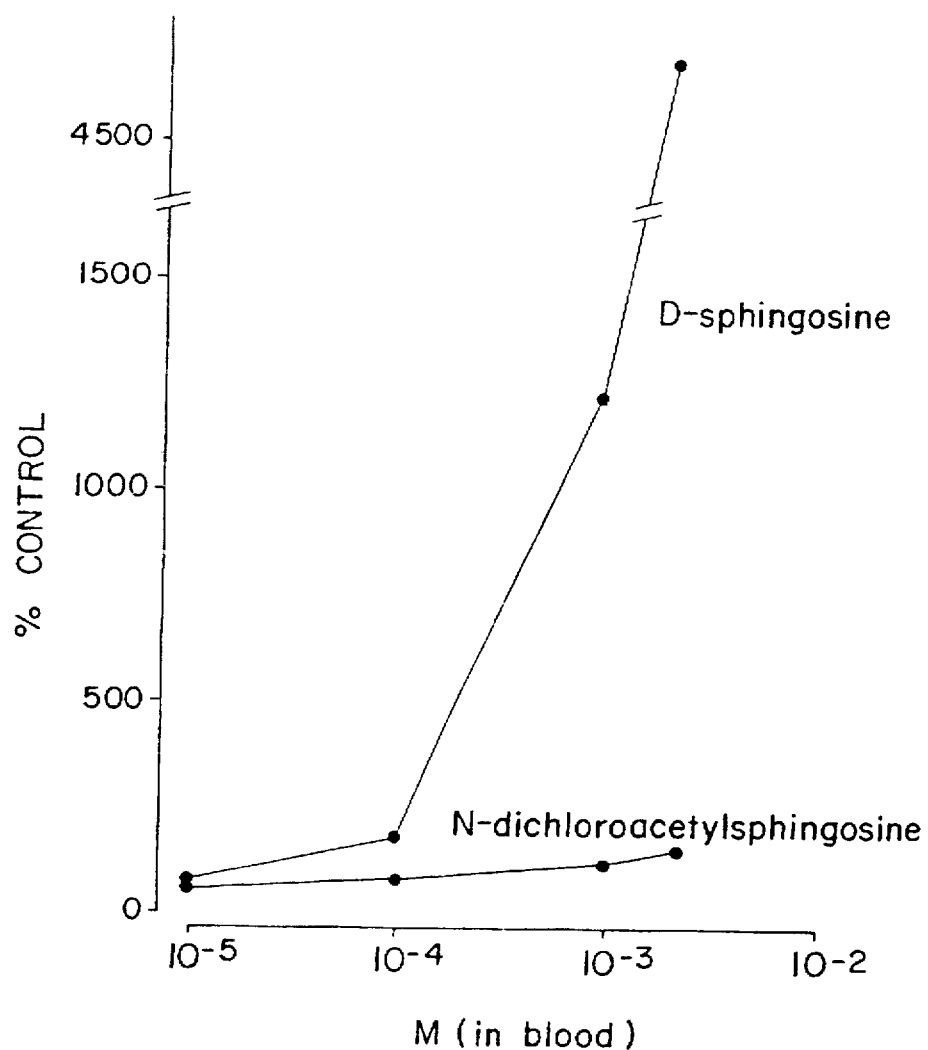
Effects of N-dichloroacetylsphingosine and D-sphingosine on haemolysis

LYSOSPHINGOLIPID DERIVATIVES

This application is a continuation of application Ser. No. 07/916,257, filed on Jul. 21, 1992, now U.S. Pat. No. 5,519,007, which is a Rule 60 continuation of Ser. No. 07/443,495 filed on Nov. 30, 1989 (now abandoned) the entire contents of which are hereby incorporated by reference.

The present invention is directed to new derivatives of lysosphingolipids free from sialic acids and more precisely N-acyllysosphingolipids corresponding to one of the two formulae:

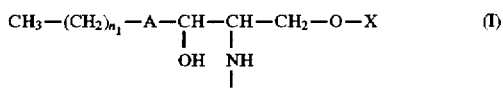

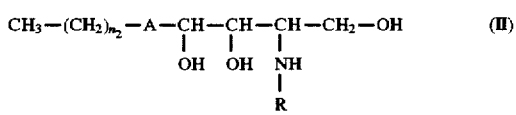

in which -A- stands for the group —CH=CH— or —CH$_2$—CH$_2$—, $n_1$ is a whole number of between 6 and 18, $n_2$ a whole number of between 11 and 15, X is a hydrogen atom or the residue of a monosaccharide or a disaccharide or phosphorylcholine and R represents an acyl radical derived from a saturated or unsaturated aliphatic carboxylic acid having between 2 and 24 carbon atoms substituted by one or more polar groups selected from the group consisting of:

chlorine, bromine and fluorine;

free hydroxy groups or hydroxy groups esterified with an organic or inorganic acid;

etherified hydroxy groups;

keto, ketal, and acetal groups derived from lower aliphatic or araliphatic alcohols;

ketoxime, aldoxime or hydrazone groups optionally substituted by lower alkyl or aralkyl groups;

free mercapto groups or mercapto groups esterified with a lower aliphatic or araliphatic acid or etherified with lower aliphatic or araliphatic alcohols;

free or esterified carboxy groups;

free sulfonic groups or sulfonic groups esterified with lower aliphatic or araliphatic alcohols;

sulfamide groups or sulfamide groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups;

and derivatives thereof with peracylated hydroxy groups, with the exception of N-(γ-amino-butyryl) sphingosine, N-(dichloroacetyl)sphingosine and N-(dichloroacetyl) dihydrosphingosine, or mixtures of said N-acyllysosphingolipids, and metal or organic base salts or acid addition salts thereof.

The invention is also directed to pharmaceutical preparations containing one or more of the above-said derivatives of N-acyllysosphingolipids or their salts as active principles with one or more pharmaceutical vehicles, and also pharmaceutical preparations containing as active principles N-(γ-amino-butyryl)sphingosine or N-(dichloroacetyl) sphingosine or N-(dichloroacetyl)dihydrosphingosine. The invention also includes the therapeutic use of these three N-acyllysosphingolipids and that of all the other N-acyllysosphingolipids mentioned above, and their mixtures and salts.

Natural sphingosines are compounds present in sphingolipids and are therefore to be considered "lysosphingolipids", which in turn are classified according to the nature of their polar structure which is linked with the primary hydroxyl group present at the C-1 position of the sphingosine. There are many different kinds of sphingolipids because of the wide variety of different oligosaccharides, single sugars, phosphate esters and other polar groups attached to this position. In sphingolipids the amino group at the C-2 position of the sphingosine is substituted by fatty acid structures; the basic amino group is therefore found as a natural amide. Since many different fatty acids and sphingosines coexist in the same sphingolipid, all natural sphingolipids must be considered homogenous as far as the polar part and complex mixtures of closely connected structures are concerned (sphingosines, fatty acids).

The compounds of the present invention are therefore particular kinds of analogues of natural sphingolipids, whose diversity consists in the presence of one single unitary acyl group on the amino group and in which such an acyl, contrary to natural products, is substituted by polar groups. The new compounds therefore represent semisynthetic sphingolipids, which can be obtained by the introduction of the acyl group R into the basic "lysosphingolipids". The term "lysosphingolipids", as used in the present application, covers both the compounds corresponding to formulae (I) and (II), but without the radical acyl R, in which the terminal hydroxyl of the aminoalcohols is in free form, as is certainly the case of formula (II), and the derivatives of formula (I), in which X is one of the said radicals, in which the terminal hydroxyl is linked glycosidically to a monosaccharide or to a di-saccharide, such as those present in some sphingolipids or to a phosphorylcholine, as in the case of lysosphingomyelin or lysodihydrosphingomyelin.

Lysosphingolipids, which serve as the base for the preparation of N-acyllysosphingolipids of the above-said formulae I and II, are preferably all those obtainable by deacylation of natural sphingolipids free from sialic acids, and therefore constitute mixtures of chemical compounds of the above formulae with carbon atom chains of varying length. The present invention also refers however to single unitary compounds corresponding to the above formulae.

One monosaccharide from which residue X is derived in formula I is preferably a pentose or a hexose, for example of the D or L series, linked by a glucoside bond α or β to the sphingosine. Special mention should be made of D-arabinose, D-xylose, D-ribose, L-ramnose, D-glucose, L-glucose, D-galactose, D-N-acetyl glucosamine, L-N-acetyl galactosamine, D-mannose, D-fructose, and digitoxose. Among the disaccharides, special mention should be made of those formed by the monoses named herein, such as saccharose, lactose, cellobiose, or maltose.

Of the sialic acid-free "natural" lysosphingolipids, which serve as bases for the new derivatives of the invention, the following must be mentioned:

the sphingosines of the formula

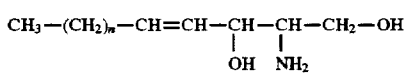

where n may take on values of between 6 and 16 the dihydrosphingosines of the formula

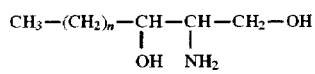

where n may take on values of between 8 and 18 the psychosines or galactosylsphingosines of the formula

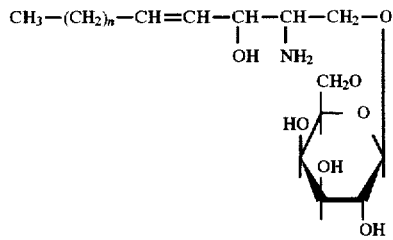

where n may take on values of between 6 and 16 the dihydropsychosines of the formula

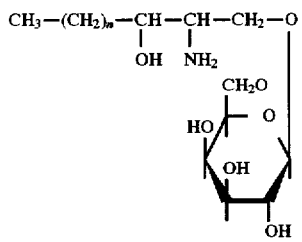

where n may take on values of between 8 and 18 the phosphorylcholine or lysosphingomyelin sphingosines of the formula

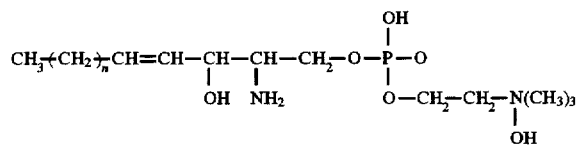

where n may take on values of between 6 and 16 the phosphorylcholine or lysodihydrosphingomyelin dihydrosphingosines of the formula

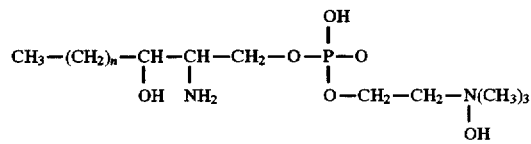

where n may take on values of between 8 and 18 the phytosphingosines of the formula

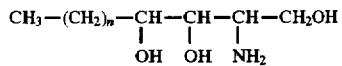

where n may take on values of between 11 and 15 the glucosylsphingosines of the formula

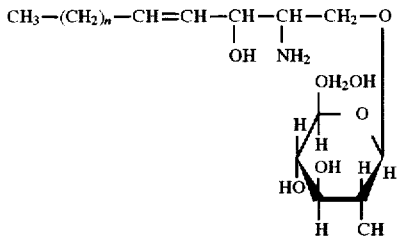

where n may take on values of between 6 and 16 the lactosylsphingosines of the formula

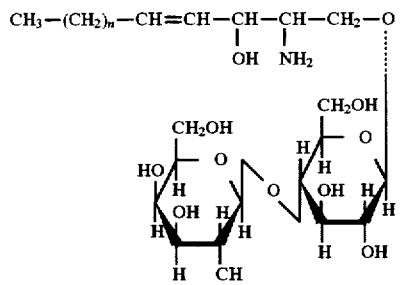

where n may take on values of between 6 and 16

These compounds can be obtained from natural sphingolipids [R. W. Leeden and R. K. Yu: Structure and Enzymic degradation of sphingolipids in Lysosomes and storage disease, pp. 105–145, Academic Press (1973)] or they can be prepared synthetically as described in the literature [Schmidt R. R.; Zimmermann P., Koko JP 62 39.597 (1987); Hasegawa Akira et al., JP 62 207.247 (1987); Umemura et al., Agric. Biol. Chem. 51 (7) (1973) - 82 (1987); Findeis M. A., J. Org. Chem. 52, pp. 2838–48 (1987); Kiso Makoto et al., Carbohydr. Res. 158, pp. 101–111 (1987); Gal A. E. et al., Chem. Phys. Lipids 42, pag. 199–207 (1986); Hay J. B. et al., Chem. Phys. Lipids, 3, pag. 59–69 (1969)].

The derivatives of the present invention, with the exception of the three specifically named hereinafter, are new compounds. It would seem that in the N-acyl residue of a few sphingolipids, as in natural acylated derivatives of sphingosines, there are present higher aliphatic hydroxyacids with a similar number of carbon atoms as the compounds of the present invention, since corresponding fatty acids have been found in their hydrolysis products. However, sphingolipids with acyl groups derived from such acids have never been isolated or described, so that the hydroxy derivatives in the N-acyl residue according to the present invention are also to be considered as being novel.

The new lysosphingolipid derivatives of the present invention have interesting pharmacological properties and more precisely an inhibiting action on protein-kinase C activation, which can have an undesirable negative effect under certain conditions of balance of the normal neurotransmission mechanisms. Protein-kinase C activation originates from an increased concentration of excitatory amino acids, such as glutamic and/or aspartic acids. Under such abnormal conditions these acids have a direct toxic action on neuronal cells. One great advantage of the products of the present invention, which sets them apart from other protein-kinase C inhibitors, such as sphingosines themselves or gangliosides, consists in their ability to prevent and combat this neurotoxic action.

Furthermore, the new derivatives are neurotoxic only at far higher doses than those which cause inhibition of protein-kinase C. The new semisynthetic sphingolipids of the present invention can be applied in therapies for various pathologies of the nervous system, such as ictus, trauma, chorea, senescence, epilepsy and neurodegenerative diseases of the nervous system, myocardial infarct and angina pectoris. The pharmacological properties of the new N-acyllysosphingolipids can be illustrated by the following experiments on N-dichloroacetylsphingosine.

Effect of Sialic Acid-Free N-acyllysosphingolipids on Protection of Neuronotrophic Effects of Excitatory Aminoacids In primary granule cell cultures, translocation and activation of protein-kinase C (PKC) can be provoked by stimulation of excitatory amino acid (EAA) receptors. Translocation of PKC can be measured by assessment of the bond sites of 4-B-[3H]-phorbol 12,13-dibutyrate [3H]-P (BtO2) in intact cells. In particular, glutamate brings about dose-dependent translocation of the bond sites of [3H]-P (BtO2) from the cytosol to the neuronal membrane. It is already known that addition of glutamate to such cultures causes cell damage, presumably mediated by the increase in $Ca^{2+}$ influx induced by glutamate and in the consequent translocation of protein-kinase C from cytosol to the neuronal membrane.

Recently, Vaccarino et al. [Proc. Natl. Acad. Sci. USA 84, 8707–8711 (1987)] reported that exposure of granule cells to the gangliosides trisialosyl-N-tetraglycosylceramide (GT1b) or monosialosyl-N-tetraglycosylceramide (GM1), inhibits the translocation and activation of PKC induced by glutamate. These glycosphingolipids do not interfere with the glutamate bond up to its high affinity recognition site or with the [3H]-P(BtO2) bond. Furthermore, these gangliosides, and particularly GT1b, offer protection from glutamate-induced cell damage. It has recently been reported [Hannun Y. A. et al., Biol. Chem. 261, 12604–12609 (1986); Merril A. H. et al., J. Biol. Chem. 261, 12610–12615 (1986); Wilson E. et al., J. Biol. Chem. 261, 12616–12623 (1986); Hannun Y. A. et al., Science 235, 670–673 (1987)] that sphingosines and correlated bases inhibit the activity and translocation of PKC.

The following experiments show studies carried out with N-dichloroacetylsphingosine, in comparison to sphingosine. In particular, their effects on PKC translocation and glutamate-induced neuronal toxicity in primary granule cell cultures were observed. Possible cytotoxic effects of the products were assessed according to their neurotoxic effects in cerebellar cells in culture, as well as hemolysis.

The sole FIGURE in the drawing shows the effects of N-dichloroacetylsphingosine and D-sphingosine on hemolysis.

MATERIALS AND METHODS
Cell Cultures:
Primary cultures were prepared with granule cells from 8-day-old Sprague-Dawley rats (Zivic Miller). These cultures have a granule cell content of >90%, 5% of GABAergic neurons [Gallo V. et al., Proc. Natl. Acad. Sci. USA 79, 7919–7923 (1982)] and <5% of glia cells [Vaccarino F. M. et al., J. Neurosci. 7, 65–76 (1987)]. The cultures were used for the experiments on the 8th and 9th days in vitro.
Compounds Added to the Cultures/Addition Methods and Parameters:
On the 8th and 9th days in vitro, sphingosines and N-dichloroacetylsphingosines at various concentrations (1–100 μM) were added to the cultures. In particular, monolayers of granule cells were pre-incubated with these compounds in Locke's solution (1 ml) for 2 hrs at 37° C. The sphingosine was dissolved in ethanol, stored as an equimolar complex with bovine serum albumin (BSA) with no fatty acids, and diluted directly with the Locke's solution used to preincubate the cells. The N-dichloroacetylsphingosine was dissolved in DMSO and diluted directly in Locke's solution (as noted above). Aliquots of the dilutions were dried in a flow of N2, after which Locke's solution was added until the desired concentration was reached.

PKC Translocation Induced by Glutamate/ Determination of the Phorbol Ester Bond [3H] with Intact Cells After 2 hours' incubation at 37° C. of the cells with or without the compounds (see above), the monolayers were washed once and the [3H]-P(BtO2) bond was assessed in the presence of 1 μM of glutamate and in the absence of $Mg^{2+}$. In particular, the granule cells cultivated in the 35 mm plates were washed once with Locke's solution (154 mM NaCl/5.6 mM KCl/3.6 mM $NaHCO_3$/2.3 mM $CaCl_2$/1 mM $MgCl_2$/5.6 mM glucose/5 mM Hepes, pH 7.4) and incubated in 1 ml of Locke's solution containing 4-B-[3H]-phorbol 12,13-dibutyrate [3H]-P(BtO)$_2$; 12.5 Ci/mmol; 1 Ci=37 GBq; New England Nuclear), in 0.1% bovine serum albumin without fatty acids (Sigma Chemical Co.). Preliminary experiments have shown that balance is reached within 10 minutes, so the monolayers were incubated with [3H]-P(BtO)$_2$ for 15 minutes at 22° C. The bond remained constant for a maximum time of 1 hour. After incubation, the cells were washed three times with cold Locke's solution, and then suspended with 0.1M NaOH. Aliquots of the suspension were then used for protein determination (9) and liquid scintillation count. The nonspecific bond was determined in the presence of 2 μM phorbol 12-tetradecanoate 13-acetate (PTA).

Glutamate-Induced Neuronal Toxicity:
Monolayers of intact granule cells were pre-incubated with various compounds at various concentrations for 2 hours at 37° C. After removal of the excess compounds and repeated washings, the cells were incubated with 50 μM glutamate in the absence of $Mg^{2+}$ for 15 minutes at room temperature. At the end of treatment with glutamate three more washings were effected, after which the monolayers were placed once more in the culture medium. Cell survival was assessed by histochemical techniques after 24 hours. In particular, cell viability was assessed after fluorescein staining, which gives green fluorescence to vital cells and red fluorescence to nonvital ones.

Cytotoxicity/Neurotoxicity and Hemolysis:
Possibile cytotoxicity of the compounds themselves was calculated by assessing the toxicity in the cerebral cultures in the absence of glutamate. The experiments and techniques used were those described above, with the difference that glutamate was omitted. The possible hemolytic effects of the compounds were also assessed. Samples of blood were taken from 4 volunteers. Each sample was subdivided into three test tubes as follows:

1. 1 ml of blood+1 ml of N-dichloroacetylsphingosine
2. 1 ml of blood+1 ml of D-sphingosine
3. 1 ml of blood+1 ml of plasma from the same volunteer (negative control)

N-dichloroacetylsphingosine and D-sphingosine were added to the samples at various concentrations (see the experiments described above). The test tubes were incubated for 45 minutes at 37° C. and then centrifuged.

The hemoglobin in the supernatant was quantified by the cyanomethahemoglobin method. In this test, the quantity of incubated hemoglobin must be the same, or smaller, than that of the negative control.

RESULTS

The tested compound inhibited glutamate-induced PKC translocation from the glutamate and proved capable of significantly reducing cell toxicity induced by glutamate. The $ED_{50}$ values of the activity of the compounds are reported in Table 1, columns 1 and 2, respectively. Table 1 (column 3) also shows results relative to the possible neurotoxicity in vitro of the compounds themselves. It should be noted that N-dichloroacetylsphingosine shows either no toxicity at all, or toxicity at significantly higher concentrations than those able to antagonize translocation induced by glutamate (column 1) as well as the neuronal toxicity induced by glutamate (column 2). Furthermore, as shown in the FIGURE in the drawing, N-dichloroacetylsphingosine, contrary to sphingosine, does not cause hemolysis.

TABLE 1

Effects of sphingosine on glutamate-induced PKC translocation (PKC inhibition), neuronal toxicity induced by glutamate (protection from glutamate) and neurotoxicity. Data refer to the $ED_{50}$ (μM)

| Compounds | PKC inhibition (μM) | Protection from glut. (μM) | Neurotoxic. in 24 hours (μM) |
|---|---|---|---|
| sphingosine | 20 | NO | 10–20 |
| N-dichloro-acetylsphingosine | 30 | 30 | >100 |

European patent application No. 0 072 286 describes some sphingosine derivatives in which the N-acyl residue is unitary and is derived from a carboxylic acid which is active on the central or peripheral nervous systems in vitro, but which has poor or no activity in vivo, due to its difficulty in overcoming the hemato-encephalic barrier and/or in reaching the peripheral organs of the nervous system. When these acids are combined by an amide bond with lysosphingolipids, they acquire the ability to overcome the hemato-encephalic barrier and to carry out their action in vivo. The disclosure of the European patent application therefore concerns the vehicling function which lysosphingolipids have on active acids of the nervous system. In the present invention, on the other hand, sphingolipids are modified by substituting their acyls with "artificial" acyls to obtain particular modifications of the biological action of the sphingolipids themselves, an action which is essentially an inhibition of protein-kinase C and is amply described in the literature (see Hannun Y. A. et al. (1986)—Sphingosine inhibition of protein-kinase C activity and of phorbol dibutyrate binding in vitro and in human platelets; J. Biol. Chem. 261, 12604–12609; Merrill A. H. et al.—Inhibition of phorbol ester-dependent differentiation of human promyelocytic leukemic (HL-60) cells by sphinganine and other long-chain bases; J. Biol. Chem. 261, 12610–12615; Wilson E. et al. (1986)—Inhibition of the oxidative burst in human neutrophils by sphingoid long-chain bases; J. Biol. Chem. 12616–12623; Hannun Y. A. et al. (1987)—Lysosphingolipids inhibit proteinkinase C: implications for the sphingolipidoses (Science 235, 670–673).

The new sphingolipid derivatives of the present invention have an advantage over known compounds able to inhibit protein-kinase C, and that is that they possess a protective effect against the toxic influence of excitatory amino acids and they are therefore suitable for use in the preparation of efficacious medicaments.

One of the acids which is active on the nervous system and is mentioned in the above-cited European patent application is also γ-aminobutyric acid, which is to be included in the group of acids characteristic of the present invention, and which is therefore not to be included among the new products of the present invention. Its therapeutic use is claimed for those indications requiring an inhibiting agent for protein-kinase C, for example those listed above.

Also excluded from the present invention as a new compound is dichloroacetyl-sphingosine described in Biochemistry, 21, 928 (1982) and N-dichloroacetyl-dihydrosphingosine described in J. Org. Chem. 28, 2157 (1963). The therapeutic use of these compounds is however claimed, as well as the pharmaceutical preparations containing them as active principles. The N-acyl radical defined above, characteristic of the new compounds according to the present invention, is derived from aliphatic acids with between 2 and 24 carbon atoms. The acids may be polybasic, but are preferably those with one single carboxy function. They are preferably straight-chained. In those radicals with branched chains, the lateral chains are preferably lower alkyl groups with a maximum of 4 carbon atoms, and especially methyl groups. The alkyls, especially those with branched chains, possess preferably a maximum of 12 carbon atoms, and especially 6 carbon atoms. The alkyl radicals are preferably saturated, but may also have double bonds, preferably between one and two.

The polar groups which substitute the N-acyl radical are preferably between 1 and 3 in number and may be the same as, or different from, each other. Compounds with alkyl radicals in the α-position are preferred, especially in those with a higher carbon atom content and/or in unsaturated ones.

The polar groups are free functions, such as hydroxy or amino groups, or functional derivatives, such as esters, ethers, ketals, etc. The esters, for example, of the hydroxy or amino groups, may be derived from acids of the aliphatic, aromatic, araliphatic, alicyclic or heterocyclic series. Such ester groups are preferably derived from therapeutically acceptable acids. The aliphatic acids are preferably lower acids with a maximum of 8 carbon atoms, such as acetic, propionic, butyric or valerianic acid, for example isovalerianic acid or their substituted derivatives, such as hydroxy acids, for example glycolic acid, or α or β-hydroxybutyric acid, lactic acid, amino acids such as natural amino acids, e.g., glycine, alanine, valine, phenylglycine, or dibasic acids, which can also be substituted, such as malonic acid, succinic acid, and maleic acid. Acids of the aromatic series are for example benzoic acid or its derivatives substituted by between 1 and 3 lower alkyl groups, hydroxy or lower alkoxy groups, or by halogens, such as chlorine, fluorine or bromine. Of the araliphatic alcohols, special mention should be made of those with one single benzene ring, such as phenylacetic or phenylpropionic acid, possibly substituted as described above. Alicyclic acids are preferably those with rings of 5 or 6 carbon atoms, such as hexanecarbonic or hexanedicarbonic acid. Of the acids of the heterocyclic series, special mention should be given to the simple ones with only one heterocyclic group, such as the derivatives of pyridine or piperidine, such as nicotinic or isonicotinic acid or α-pyrrolidine carbonic acid.

Of the alcohols which can form the etherifying component of hydroxy groups or etherified mercapto groups, those of the aliphatic series can be mentioned in particular and especially those with a maximum of 12 and especially 6 carbon atoms, or of the araliphatic series having preferably one single benzene ring, possibly substituted by 1–3 lower alkyl groups ($C_{1-4}$) for example methyl groups and with a maximum of 4 carbon atoms in the aliphatic chain, or of alcohols of the alicyclic or aliphatic-alicyclic series having only one cycloaliphatic ring and a maximum of 14 carbon atoms or of the heterocyclic series having a maximum of 12 and especially 6 carbon atoms and only one heterocyclic ring containing a heteroatom chosen from the group formed by N, O and S. These alcohols may be substituted or unsubstituted, especially by functions chosen from the group formed by hydroxy, amino or alkoxy groups, with a maximum of 4 carbon atoms in the alkyl, carboxy or carbalkoxy groups with a maximum of 4 atoms in the alkyl residue, alkylamines or dialkylamines with a maximum of 4 carbon atoms in the alkyl portion, and may be saturated or unsaturated, especially with only one double bond.

The alcohols may be monovalent or polyvalent, in particular bivalent. Of the alcohols of the aliphatic series, special mention should be given to those lower alcohols with a maximum of 6 carbon atoms, such as methyl alcohol, ethyl alcohol, propyl alcohol and isopropyl alcohol, normal butyl alcohol, isobutyl alcohol, tertiary butyl alcohol, and of the bivalent alcohols, ethylene glycol and propylene glycol. Of the alcohols of the araliphatic series, particular mention should be made of those with only one benzene residue, such as benzyl alcohol and phenethyl alcohol. Of the alcohols of the alicyclic series, preference should be given to those with only one cycloaliphatic ring, such as cyclohexyl alcohol (cyclohexanol).

Of the alcohols of the heterocyclic series, special mention should be made of tetrahydrofuranol or tetrahydropyranol.

The alcohols can also be substituted, for example, by amino functions, such as amino alcohols, for example those with a maximum of 4 carbon atoms and especially amino acohols with a dialkyl ($C_{1-4}$) amino group, such as diethylaminoethanol.

Lower aliphatic or araliphatic alcohols with a maximum of 4 carbon atoms in the aliphatic part and a benzene group possibly substituted as previously described are preferable. The alkyl or aralkyl groups which may substitute on the amino groups should preferably have a maximum of 4 carbon atoms, and this maximum is also present in all the aliphatic groups qualified as "lower" in the above definitions. Lower alkyl groups, which can substitute on the amino groups to form saturated heterocyclic groups, are mainly constituted by those with between 4 and 5 carbon atoms. Of the lower saturated acids with the said number of carbon atoms, from which the N-acyl group is derived, note is to be made of those which are halogenated and especially chlorine or fluorine derivatives, and particularly those which have a dichloride in the α-position. Examples thereof are the following:

dichloroacetic acid, trichloroacetic acid and its fluoride and bromide analogues, 2,2-dichloropropionic acid, 2,3-dichloropropionic acid, 2,2,3-trichloropropionic acid, normal 2,2-dichlorobutyric acid, 2,2-dichlorovalerianic acid, 2-chloroisovalerianic acid, 2,3-dichlorovalerianic acid, pentafluoropropionic acid, 3,3-dichloropivalic acid, 3-chloro-2,2-dimethylpropionic, chloro-difluoro-acetic acid, 2,2-dichlorocapronic acid, 2-monochloropropionic acid, normal 2-monochlorobutyric acid, 2-monochlorovalerianic acid, 2-monochlorocapronic acid and their fluoride and bromide analogues, 2-chloropalmitic acid, 2-chlorostearic acid, 2-chlorooleic acid, 2-chlorolauric acid, 2-chlorobehenic acid, 4-chlorophenoxyacetic acid, 2-hydroxypropionic acid (lactic acid), 3-hydroxypropionic acid, 2-hydroxybutyric acid, 2-hydroxyvalerianic acid, 3-hydroxyvalerianic acid, 2,3-dihydroxybutyric and 2,3-dihydroxyvalerianic acids. Also included are ethers thereof with lower aliphatic alcohols having a maximum of 4 carbon atoms or esters between the hydroxy groups and lower aliphatic acids with a maximum of 4 carbon atoms. Other examples include one of the above-said acids of the aromatic, araliphatic, alicyclic or heterocyclic series, methoxyacetic acid, 12-hydroxystearic acid, 2-(4-hydroxyphenoxy)propionic acid, 2-hydroxyisocapronic acid, 2-hydroxyisobutyric acid, 4-fluorophenoxyacetic acid, ethoxyacetic acid, pyruvic acid, acetacetic acid, levulinic acid and their ketals with lower aliphatic alcohols having a maximum of 4 carbon atoms and/or their oximes or substituted oximes with alkyl groups having a maximum of 4 carbon atoms, mercaptoacetic acid, 2-mercaptopropionic acid, 2-mercaptobutyric acid, 2-mercaptovalerianic acid and their ethers with lower aliphatic monovalent alcohols with a maximum of 4 carbon atoms or their esters with lower aliphatic acids having a maximum of 4 carbon atoms, 2-mercaptolauric, oleic and palmitic acids and their esters or ethers of the above-said type, malonic acid, glutaric acid, monomethylglutaric acid, 3-hydroxy-3-methylglutaric acid, maleic acid, malic acid, succinic acid, fumaric acid, azelaic acid and their esters with aliphatic alcohols having a maximum of 4 carbon atoms, sulfoacetic acid, 2-sulfopropionic acid, 2-sulfobutyric acid, 2-sulfovalerianic acid and their esters with aliphatic alcohols having a maximum of 4 carbon atoms. Among the higher acids substituted by sulfonic groups can be mentioned 2-sulfolauric acid, 2-sulfooleic acid, 2-sulfopalmitic acid, 2-sulfostearic acid and their esters as noted above, as well as the corresponding sulfamides or sulfamides substituted by lower alkyl groups with a maximum of 4 carbon atoms or by alkyl groups with 4 or 5 carbon atoms, acetic, propionic, butyric and valerianic (valeric) acids substituted in the α-position by an alkylsulfoxide or alkylsulfonic group in which the alkyl has a maximum of 4 carbon atoms, cyanoacetic acid, 2-cyanopropionic acid, 2-cyano-butyric acid, 2-cyanovalerianic acid, aminoacetic acid, 2-aminopropionic acid, 2-aminobutyric acid, 3-aminobutyric acid, 2-aminovalerianic acid, 4-aminovalerianic acid and their derivatives with one or two alkyls substituting the amino hydrogen with a maximum of 4 carbon atoms or with an alkylene group having 4 or 5 carbon atoms. Derivatives thereof with the amino group acylated by a lower aliphatic acid with between 1 and 4 carbon atoms or with one of the aromatic, alicyclic or heterocyclic acids mentioned above, or groups of quaternary ammonium salts of tertiary amino groups derived from alkyls having a maximum of 4 carbon atoms, ethionine, dimethylglycine, 3-diethylaminopropionic acid, carnitine and cysteic acid can also be employed.

It is possible to prepare the metal salts of the new compounds according to the present invention which have free carboxy functions, and these too form part of the invention. Also constituting part of the invention are salts obtained by the addition of acids of N-acyllysosphingolipids containing a free amino function, for example derivatives with amino acids. Among the metal salts which can be particularly mentioned are those which can be used for therapeutic purposes, such as salts of alkali or alkaline earth metals, for example potassium, sodium, ammonium, calcium and magnesium salts or salts of earth metals such as aluminum, and also salts of organic bases, for example of primary, secondary or tertiary aliphatic or aromatic or heterocyclic amines, such as methylamine, ethylamine, propylamine, piperidine, morpholine, ephedrine, furfurylamine, choline, ethylenediamine and aminoethanol. Of the acids capable of giving salts by acid addition of the N-acyllysosphingolipid derivatives according to the invention, should be mentioned in particular hydrogen acids, such as hydrochloric acid, hydrobromic acid, phosphoric acid, sulfuric acid, lower aliphatic acids with a maximum of 7 carbon atoms, such as formic, acetic or propionic acids, or succinic or maleic acids. Therapeutically unusable acids or bases, such as picric acid, can be used for the purification of the new N-acyl-lysosphingolipid derivatives and also form part of the invention. Due to the close relationship between the derivatives of the invention in their free form and in the form of their salts, the present description of the invention refers to either form indiscriminately, unless otherwise stated.

The new N-acyllysosphingolipid derivatives of the present invention can be prepared in a known way, and more precisely by acylation of the above-mentioned compounds.

With N-acyl lysosphingolipids, it is also possible, if desired, to functionally convert polar groups present in the introduced N-acyl group, for example to esterify hydroxy groups, alkylate amino groups, or to convert carbonyl groups into O-alkylhydroxyamino derivatives. Should one wish to prepare peracylates of the compounds obtained, it is necessary to effect a further acylation of the hydroxy groups under conditions conducive to such a reaction. All of the hydroxyls can be acylated, those of the sphingosine chain itself as well as of the sugars which may be present. The peracylated derivatives thus obtained have the same properties as the derivatives with free hydroxyls and may be used in therapies for the same purposes. The hydroxy peracylates of the new N-acyl lysosphingolipids are particularly derived from aliphatic acids having a maximum of 8 carbon atoms and such acids may be saturated, unsaturated, mono- or dibasic. Special mention should be made of peracetylates, perpropionylates, perbutyrylates, permaleinylates, permalonylates and persuccinylates.

Among the new N-acyllysosphingolipids according to the present invention, special note should be taken of the following derivatives: sphingosine derivatives with N-acyls of the above specific acids; dihydrosphingosine derivatives with N-acyls of said acids; psychosine derivatives with acyls of said acids; dihydropsychosine derivatives with N-acyls of said acids; lysosphingomyelin derivatives with N-acyls of the acids; lysodihydrosphingomyelin derivatives with N-acyls of the acids; phytosphingosine derivatives with N-acyls of the acids; and in particular N-dichloroacetylsphingosine, N-chloroacetylsphingosine, N-hydroxyacetylsphingosine, N-trifluoroacetylsphingosine, N-trichloroacetylsphingosine, N-mercaptoacetylsphingosine, N-maleylsphingosine, N-12-hydroxystearoylsphingosine, N-2-hydroxybutyroylsphingosine, N-fluoroacetylsphingosine, N-difluoroacetylsphingosine, N-3-aminopropionylsphingosine, N-cyanoacetylsphingosine, N-3-diethylaminopropionylspingosine, N-aminoacetylsphingosine, N-dichloroacetylglucosylsphingosine, N-chloroacetylglucosylsphingosine, N-trifluoroacetylglucosylsphingosine, N-fluoroacetylglucosylsphingosine, N-dichloroacetyllactosylsphingosine, N-trifluoroacetyllactosylsphingosine, N-3-diethylaminopropionyllactosylsphingosine and peracylates of these compounds of the type described above, and the analogues of all of these compounds derived from the other specific lysosphingolipids mentioned previously.

The procedure of the present invention comprises acylating a sphingosine derivative of one of the formulae (I) and (II) in which, however, in place of R there is a hydrogen atom, or mixtures of these compounds, optionally following temporary protection of the free functional groups in the acylating component, with an aliphatic acid having between 2 and 24 carbon atoms, substituted by one or more polar groups chosen from the group constituted by:

chlorine, bromine and fluorine;

free hydroxy groups or hydroxy groups esterified with an organic or inorganic acid;

etherified hydroxy groups;

keto, ketal, and acetal groups derived from lower aliphatic or araliphatic alcohols;

ketoxime, aldoxime or hydrazone groups optionally substituted by lower alkyl or aralkyl groups;

free mercapto groups or mercapto groups esterified with a lower aliphatic or araliphatic acid or etherified with lower aliphatic or araliphatic alcohols;

free or esterified carboxy groups;

free sulfonic groups or sulfonic groups esterified with lower aliphatic or araliphatic alcohols;

sulfamide groups or sulfamide groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups.

If desired, the compounds having hydroxy groups may be peracylated and/or optionally converting the polar groups substituted on the N-acyl group one into the other. If desired, the products may be converted into suitable salts.

N-acylation, according to the above procedure, can be carried out in a conventional way, for example by reacting the starting products with an acylating agent, especially with a reactive functional derivative of the acid, the residue of which is to be introduced. It is thus possible to use, as a functional derivative of the acid, a halogenide or an anhydride. Acylation is carried out preferably in the presence of a tertiary base, such as pyridine or collidine. It is possible to work under anhydrous conditions, at room temperature, or by heating, or the Schotten - Baumann method can also be used to advantage under aqueous conditions in the presence of an inorganic base. In some cases it is also possible to use esters of the acids as reactive functional derivatives. Acylation can be effected by methods using activated carboxy derivatives as are used in peptide chemistry, for example the mixed anhydride method, or derivatives obtainable with carbodiimide derivatives or isoxazole salts.

Of the many preparation methods, the most appropriate are the following:

1. reaction of the lysosphingolipid derivative with the azide of the acid;
2. reaction of the lysosphingolipid derivative with an acylimidazole of the acid obtainable from the acid with N,N'-carbonyldiimidazole;
3. reaction of the lysosphingolipid derivative with a mixed anhydride of the acid and of trifluoroacetic acid;
4. reaction of the lysosphingolipid derivative with the chloride of the acid;

5. reaction of the lysosphingolipid derivative with the acid in the presence of a carbodiimide (for example dicyclohexylcarbodiimide) and possibly a substance such as 1-hydroxybenzotriazol;
6. reaction of the lysosphingolipid derivative with the acid by heating;
7. reaction of the lysosphingolipid derivative with a methyl ester of the acid at a high temperature;
8. reaction of the lysosphingolipid derivative with a phenol ester of the acid, for example an ester with para-nitrophenol;
9. reaction of the lysosphingolipid derivative with an ester derived from the exchange between a salt of the acid and 1-methyl-2-chloropyridinium iodide or similar products.

In the particular case of the preparation of products derived from acids containing free hydroxy or mercapto or carboxy groups, or primary or secondary amino groups, it is preferable to protect such groups during the acylation reaction, preferably using the protection methods used in peptide chemistry. Such protective groups must naturally be easily cleavable at the end of the reaction, such as the phthaloyl group or the benzyloxycarbonyl group, which serves to protect the amino group. Thus, for example, while preparing derivatives containing 4-aminobutyric acid, one should first prepare a derivative of this acid where the amino group is bound to the phthaloyl group and after acylation with the lysosphingolipid derivative the phthaloyl group is eliminated by hydrazinolysis. The benzyloxycarbonyl group can be eliminated by hydrogenolysis. This residue can also be used to protect the hydroxy groups. The carboxy group can be protected by esterification, for example with the alcohols used in peptide chemistry. Acylation of the hydroxy groups of the saccharide part which may be present in the N-acyllysosphingolipids of the present invention and possibly together with hydroxy groups present as polar groups in the N-acyl residue can be effected in the known way, for example by acylation with a halogenide or an anhydride of the acid used for acylation, in the presence of a tertiary base, such as pyridine or collidine. The peracylated derivatives mentioned above are obtained in this way. In the compounds obtained according to the above procedure, it is possible to convert the functions present in the N-acyl group between them. For example, it is possible to acylate hydroxy groups, possibly selectively, leaving other hydroxy groups intact, such as saccharide groups, using mild reagents and conditions. It is possible to etherify the hydroxy or mercapto groups, to alkylate the amino groups or to acylate the amino groups. Finally, in all of the compounds obtainable by the said procedures and which present salifiable groups, such groups can be salified in the known way.

The invention also includes modifications in the preparation procedure for the new derivatives, in which a procedure can be interrupted at any one stage or in which the procedure is begun with an intermediate compound and the remaining stages are then carried out, or in which the starting products are formed in situ. Other objects of the present invention are pharmaceutical preparations containing as active substance one or more of the new lysosphingolipid derivatives, and, in particular, those already pointed out, and also N-dichloroacetylsphingosine, N-dichloroacetyldihydrosphingosine, N-γ-aminobutyrylsphingosine.

The pharmaceutical preparations mentioned here may be preparations for oral, rectal, patenteral, local or transdermal use. They are therefore in solid or semisolid form, for example pills, tablets, gelatin capsules, capsules, suppositories, or soft gelatin capsules. For parenteral use it is possible to use those forms intended for intramuscular, subcutaneous or transdermal administration, or suitable for infusions or intravenous injections and these may therefore be presented as solutions of the active compounds or as freeze-dried powders of the active compounds to be mixed with one or more pharmaceutically acceptable excipients or diluents, convenient for use as stated and having an osmolarity which is compatible with the physiological fluids. For local use preparations in the form of sprays can be considered, for example nasal sprays, creams or ointments for topical use or suitably treated plasters for transdermal administration. The preparations of the invention can be administered to man or animals. They contain preferably between 0.01% and 10% by weight of the active component in the case of solutions, sprays, ointments and creams and between 1% and 100% by weight, preferably between 5% and 50% by weight, of the active compound in the case of solid form preparations. The dosage to be administered depends on individual indications, on the desired effect and on the chosen administration route. The daily dosage for administration to man by injection or the transdermal or oral route of the N-acyllysosphingolipids of the present invention varies between 0.05 mg and 5 mg of active substance per kg of body weight.

The following Examples 6–24 illustrate the preparation of the new derivatives according to the invention and Examples 25–28 illustrate the pharmaceutical preparations. Examples 1–5 illustrate the preparation of the starting substances needed to carry out the procedure of the invention.

EXAMPLE 1

Preparation of Psychosine Tartrate (FG-S2) by Extraction from Bovine Brain Tissue A quantity of bovine brain is homogenized in phosphate buffer at pH 6.8; 2 volumes of methylene chloride are then added and the resulting mixture is then centrifuged.

The lower phase is separated and kept at a temperature of 0° for a few days; a solid is separated (Cerosfing) which is then filtered and vacuum dried. Cerosfing contains about 30% of cerebrosides.

1 kg of Cerosfing is solubilized with 3 liters of ice cold acetic acid in a suitable reactor by heating to approximately 60° C.

After complete solubilization, it is left at room temperature overnight. The precipitate is then gathered and with this precipitate the operation is repeated once again. The new precipitate is washed with acetone and vacuum dried (FG-S1). 1000 g of FG-S1 are loaded into a thermostatic reactor (130° C.) with 7200 ml of n-BuOH and 480 ml of $H_2O$.

The mixture is refluxed and 560 gr of KOH are slowly added after being solubilized in 320 ml of $H_2O$. When all the KOH has been added, it is reacted for 5 hours by reflux. It is cooled to 35° C. and 6000 ml of $H_2O$ are added; the two phases are left to separate. The lower phase is eliminated. The upper phase is washed 5 times with 3000 ml of KOH 1N. The lower phases are discarded.

5000 ml of $H_2O$ are then added and the pH is brought to 7.3–7.5 with about 250 ml of $H_2SO_4$ 5N. The lower phase is discarded. It is washed with 2000 ml of phosphate buffer 0.1M (pH 7.2) in 1.25% saline and then with another 2500 ml of 2.5% saline. The solution is concentrated to 2000 ml and then 3000 ml of n-hexane, 2000 ml of methanol and 700 ml of $H_2O$ are added in which 250 grams (gr) of tartaric acid have been dissolved.

The lower phase is separated and set aside, and the upper phase is washed with 2×500 ml of MetOH/H$_2$O 75:25.

The upper phase is then eliminated. The first two lower phases are then united and 1500 ml of H$_2$O are added and partitioned with 2000 ml of n-hexane. The n-hexane phase is counterwashed with the third lower phase after the addition of 250 ml of H$_2$O. The hexane is discarded.

To the mixture of lower phases are added 1250 ml of H$_2$O and 750 ml of CHCl$_3$ and the MetOH/H$_2$O phase is washed with 2×400 ml of CHCl$_3$/MetOH 50:20. To the mixture of three lower phases are added 1250 ml of H$_2$O and 750 ml of CHCl$_3$ and the MetOH/H$_2$O phase is washed with 2×400 ml of CHCl$_3$/MetOH 50:2. The three lower phases are counterwashed with 1000 ml of MetOH/H$_2$O 1:1 and to the mixture of two lower phases are added 500 ml of CHCl$_3$ and NaOH 10N to a pH of 12. The procedure is repeated with 250 ml of CHCl$_3$. The upper phase is discarded.

The mixture of lower phases is washed with 1000 ml of MetOH/saline, 2.5% 1:1 and then with 500 ml of 2.5% NaCl.

The water content is removed with anhydrous Na$_2$SO$_4$. It is precipitated in 5 volumes of acetone, containing 150 gr of tartaric acid. It is filtered, and 500 gr of psychosine tartrate are obtained (FGS2).

Thin layer chromatography (silica gel):
Solvent: chloroform/methanol/H$_2$O/NH$_4$OH (70:35:5:1) Rf=0.5

EXAMPLE 2

Psychosine Base 50 gr of di FG-S2 is solubilized in 500 ml of methanol and then treated at room temperature with 100 ml of NH$_4$OH (32%).

It is left under agitation overnight. It is filtered and the precipitate washed with methanol. The methanol solutions are treated with an equal volume of saline and then partitioned with 200 ml of CHCl$_3$. An oily lower phase phase is separated which is then further purified by silica gel chromatography.

The elution solvents are:

1) chloroform
2) chloroform/methanol/NH$_4$OH 85:15:1
3) chloroform/methanol/NH$_4$OH 65:30:5.

The product (20 g) is chromatographically pure.
Thin layer chromatography (silica gel):
Solvent: chloroform/methanol/H$_2$O/NH$_4$OH (70:35:5:1) Rf=0.5

EXAMPLE 3

Sphingosine Sulfate (FG-S3)

500 gr of FG-S2 is dispersed in 2000 ml of methanol and to this dispersion are added 1500 gr of p-toluenesulfonic acid (monohydrate) dissolved in 2000 ml of methanol. It is left to reflux in a reactor for 7 hours at 90° C.

It is cooled to 5°–10° C. and 7500 gr of ice and about 800 ml of NaOH 10N are added to give a pH of 12. The sphingosine base is extracted with 700 ml of CH$_2$Cl$_2$ and the upper phase is washed with 2×500 ml of CH$_2$Cl$_2$/EtOH 60:30.

The upper phases are rewashed by reflux in three separating funnels each time using 500 ml of saline 2.5%/EtOH 75:25.

The upper phases are discarded. The mixture of lower phases is spin-dried.

The residue is gathered with 1500 ml of isopropanol and heated to 50° C. to favor solubilization. The solution thus obtained is treated drop by drop with H$_2$SO$_4$ 2M (in isopropanol), until Congo red neutralization thermostating to 25° C. The precipitate is left to separate at room temperature and then at 4° C. The precipitate is then washed with acetone and dried in A.V. at 40° C. for 60 hrs.

Yield: 250 g.

Thin layer chromatography (silica gel):
Solvent: chloroform/methanol/H$_2$O/NH$_4$OH (80:20:1.7:0.3) - Rf=0.65

EXAMPLE 4

Sphingosine Base 50 gr of FG-S3 are solubilized in 300 ml of methanol and then treated at room temperature with 100 ml of NH$_4$OH (32%).

It is refluxed for 1 hour, then left to rest over-night at room temperature.

The precipitate is filtered and washed with 100 ml of methanol.

The mixture of methanol solutions is concentrated with an equal volume of saline and then partitioned with 100 ml of CHCl$_3$.

A lower phase is separated and then further purified by silica gel chromatography.

The elution solvents are:

1) chloroform
2) chloroform/methanol/NH$_4$OH 90:10:1
3) chloroform/methanol/NH$_4$OH 70:25:5

Thin layer chromatography (silica gel):
Solvent: chloroform/methanol/H$_2$O/NH$_4$OH 32% (80:20:1.7:0.3)

EXAMPLE 5

Lyso Sphingomyelin 30 gr of sphingomyelin (from bovine brain) are treated with 180 ml of a mixture (1:1) of n-butanol/HCl 6N.

It is placed in a carefully thermostated bath at 100° C. for 45 min, then left to cool, washed twice with an equal volume of water containing 10% of n-butanol.

The aqueous solutions are washed again with 10 ml of n-butanol.

The butanol solutions are concentrated together to a small volume with a rotary evaporator, under reduced pressure at a temperature of about 40° C.

The residue is treated with 1 liter of acetone and the filtered precipitate is vacuum dried.

Yield 7.5 g.

The raw product thus obtained is purified by silica gel chromatography. The separation solvent is chloroform/methanol/(NH$_4$)$_2$CO$_3$ 1.6% (60:50:12).

The pure fractions are gathered, corresponding (thin layer chromatography) to Rf 0.1 in the solvent chloroform/methanol/acetic acid/H$_2$O, 25:15:4:2.

EXAMPLE 6

N-maleyl Sphingosine 5.0 gr of sphingosine (16.70 mM), prepared according to example 4, are reacted in 100 ml of pyridine with 1.7 gr of maleic anhydride (17.70 mM). The reaction product is kept at room temperature for 24 hrs, the solvent is evaporated and then the raw product is purified by chromatography, using a silica gel column and eluting with a mixture of methylene/ methanol chloride (85:15).

It is evaporated and crystallized from ethanol (95%). The product is vacuum dried, thus obtaining a solid which does not melt, but carbonizes at 228°–230° C.

Yield 4.0 g.

Thin layer chromatography (silica gel), using as eluent the mixture formed by chloroform/methanol/water 32% (70:30:2), presents one single band at Rf=0.40.

EXAMPLE 7

N-(3-chloropivaloyl) Sphingosine 5.0 gr of sphingosine (16.70 mM), prepared according to example 4, are treated with 2.7 gr of 3-chloropivaloyl chloride (17.54 mM) and 3.5 gr of triethylamine (25.11 mM) in 150 ml of chloroform, at room temperature for 24 hrs.

The chloroform solution is washed several times with water, and then anhydrated on sodium sulfate, filtered and evaporated to dryness under reduced pressure.

The residue is thrice crystallized from ethyl ether and vacuum dried. A white product is obtained with melting point=41° C.

Yield 4.2 g.

Thin layer chromatography (silica gel), using as eluent the mixture formed by methylene chloride/ethyl acetate/ methanol (70:30:10), presents one single band at Rf=0.58.

EXAMPLE 8

N-tribromoacetyl Psychosine 5.0 gr of psychosine (10.83 mM), prepared according to example 2, are treated with 3.4 gr of tribromoacetic acid (11.37 mM) and 2.7 gr of dicyclohexylcarbodiimide (13.00 mM) in 150 ml of N,N-dimethylformamide at 60° C. for 24 hrs.

The solvent is evaporated and then the residue is gathered in chloroform and kept at –20° C. overnight. The organic solution is filtered and evaporated under reduced pressure, and the residue is purified by preparative chromatography, using a silica gel column and eluting with a mixture of methylene chloride/methanol (80:20).

The product is evaporated, thrice crystallized from ethyl acetate and vacuum dried, obtaining a solid which melts at 219°.

Yield 3.5 g.

Thin layer chromatography (silica gel), using as eluent the mixture formed by chloroform/methanol/water/ammonia 32% (80:20:1.7:0.3), presents one single band at Rf=0.61.

EXAMPLE 9

N-dichloroacetylpsychosine 5.0 gr of psychosine (10.8 mM), prepared according to example 2, are treated with 60 ml of chloroform. 2.25 ml of triethylamine (16.23 mM) and 2.05 gr of dichloroacetyl chloride (13.9 mM) are then added and the mixture is then kept at room temperature for 24 hrs.

The chloroform solution is washed with water several times and then anhydrated on sodium sulfate, filtered and evaporated to dryness under reduced pressure.

The residue thus obtained is purified by preparative chromatography, using as eluent a mixture of chloroform/ methanol/water (110:25:0.3). It is twice crystallized from acetonitrile and vacuum dried. A white product is obtained with a melting point of 161° C.

Yield 5.9 g.

Thin layer chromatography (silica gel), using as eluent the mixture formed by chloroform/methanol/water (110:40:6), presents one single band at Rf=0.7.

EXAMPLE 10

N-dichloroacetyl Lysosphingomyelin 5.0 gr of lysosphingosine (10.35 mM), prepared according to example 5, are treated in 60 ml of chloroform, with 2.25 ml of triethylamine (16.23 mM) and 2.05 gr of dichloroacetyl chloride (13.9 mM) at room temperature for 24 hrs.

The chloroform solution is washed with water several times, anhydrated on sodium sulfate, and then evaporated to dryness under reduced pressure.

The residue thus obtained is purified by preparative chromatography, using as eluent a mixture of chloroform/ methanol/water/isopropanol (90:10:4:1.6).

Yield 6 g.

Thin layer chromatography (silica gel), using as eluent the mixture formed by chloroform/methanol/water/acetic acid (25:15:2:4), presents one single band at Rf=0.25.

EXAMPLE 11

N-trichloroacetyl Sphingosine 5.0 gr of sphingosine (16.70 mM) prepared according to example 4, are treated in 100 ml of chloroform, with 3.5 ml of triethylamine (25.11 mM) and 3.9 gr of trichloroacetyl chloride (21.44 mM) at room temperature for 24 hrs.

The chloroform solution is washed with water several times, anhydrated on sodium sulfate, and then evaporated to dryness under reduced pressure.

The residue is crystallized from acetonitrile and then vacuum dried.

A white product is obtained with a melting point of 82° C.

Yield 6.5 g.

Thin layer chromatography (silica gel), using as eluent the mixture formed by methylene chloride/ethyl acetate/ methanol (70:30:10), presents one single band at Rf=0.7.

EXAMPLE 12

N-dichloroacetyl Sphingosine 5.0 gr of sphingosine (16.70 mM) prepared according to example 4, are treated in 100 ml of chloroform, with 3.5 ml of triethylamine (25.11 mM) and 3.2 gr of dichloroacetyl chloride (21.45 mM) at room temperature for 24 hrs.

The chloroform solution is washed with water several times, anhydrated on sodium sulfate, and then evaporated to dryness under reduced pressure. The residue is purified by preparative chromatography, using as eluent a mixture of chloroform/methanol (90:10).

It is twice crystallized from acetonitrile and then vacuum dried. A crystalline product is obtained with melting point 97° C.

Yield 7.0 g.

Thin layer chromatography (silica gel), using as eluent the mixture formed by methylene chloride/ethyl acetate/ methanol (70:30:10), presents one single band at Rf=0.48.

EXAMPLE 13

N-monochloroacetyl Sphingosine 5.0 gr of sphingosine (16.70 mM) prepared according to example 4, are treated in 100 ml of chloroform, with 3.5 ml of triethylamine (25.11 mM) and 2.65 gr of monochloroacetyl chloride (21.44 mM) at room temperature for 24 hrs.

The chloroform solution is washed with water several times, anhydrated on sodium sulfate, and then evaporated to dryness under reduced pressure. The residue thus obtained is purified by preparative chromatography, using as eluent a mixture of chloroform/methanol (90:10).

It is crystallized twice from isopropyl ether and then vacuum dried. A crystalline product is obtained with a melting point of 88° C.

Yield 6.0 g.

Thin layer chromatography (silica gel), using as eluent the mixture formed by ethyl acetate/methanol (80:20), presents one single band at Rf=0.67.

EXAMPLE 14

N-(12-hydroxystearoyl) Sphingosine 3.0 gr of sphingosine (10.01 mM) prepared according to example 4, are treated with 3.2 gr of DL-12-hydroxystearic acid (10.51 mM) and 2.5 gr of dicyclohexylcarbodiimide (12.01 mM) in 70 cc of N,N-dimethylformamide at 60° C. for 24 hrs.

The solvent is evaporated and then the residue is gathered in chloroform and kept at −20° C. overnight. The organic solution is filtered and evaporated under reduced pressure and the residue is purified by preparative chromatography, using a silica gel column and eluting the mixture with methylene chloride/ethyl acetate/methanol (70:30:3).

The product is evaporated and crystallized three times, obtaining a solid which melts at 104° C.

Yield 3.5 g.

Thin layer chromatography (silica gel), using as eluent the mixture formed by methylene chloride/ethyl acetate/methanol (70:30:10), presents one single band at Rf=0.40.

EXAMPLE 15

N-methoxyacetyl Sphingosine 3.0 gr of sphingosine (10.01 mM) prepared according to example 4, are treated with 0.95 gr of methoxyacetic acid (10.51 mM) and 2.5 gr of di-cyclohexylcarbodiimide (12.01 mM) in 70 ml of N,N-dimethylformamide at 60° C. for 24 hrs. The solvent is evaporated and then the residue is gathered in chloroform and kept at −20° C. overnight.

The organic solution is filtered and evaporated under reduced pressure, and the residue is purified by preparative chromatography, using a silica gel column and eluting with a mixture of methylene chloride/ethyl acetate/methanol (70:30:10).

The product is evaporated and crystallized three times from ethyl ether, obtaining a product which melts at 104° C.

Yield 3.2 g.

Thin layer chromatography (silica gel), using as eluent the mixture formed by methylene chloride/ethyl acetate/methanol (70:30:10), presents one single band at Rf=0.45.

EXAMPLE 16

N-cyanoacetyl Sphingosine 5.0 gr of sphingosine (16.70 mM) prepared according to example 4, are treated with 1.5 gr of cyanoacetic acid (17.54 mM) and 4.1 gr of dicyclohexylcarbodiimide (20.04 mM) in 100 ml of N,N-dimethylformamide at 60° C. for 24 hrs.

The solvent is evaporated and then the residue is gathered in CHCl$_3$ and kept at −20° C. overnight. The solid is filtered and the raw product purified by chromatography using a silica gel column and eluting with a mixture of methylene chloride/ethyl acetate/methanol (70:30:2).

The product is evaporated and crystallized three times from ethyl acetate and vacuum dried, obtaining a solid which melts at 113° C.

Yield 3.0 g.

Thin layer chromatography (silica gel), using as eluent the mixture formed by methylene chloride/ethyl acetate/methanol (70:30:10), presents one single band at Rf=0.46.

EXAMPLE 17

N-difluoroacetyl Sphingosine 5.0 gr of sphingosine (16.70 mM) prepared according to example 4, are treated with 1.7 gr of difluoroacetic acid (17.70 mM) and 4.1 gr of dicyclohexylcarbodiimide (20.04 mM) in 100 ml of N,N-dimethylformamide at 60° C. for 24 hrs.

The solvent is evaporated and then the residue is gathered in chloroform and kept at −20° C. overnight. The solid is filtered and purified by chromatography, using a silica gel column and eluting with a mixture of methylene chloride/ethyl acetate (70:30).

It is evaporated and thrice crystallized from ethyl ether and vacuum dried, obtaining a solid which melts at 87° C.

Yield 5.0 g.

Thin layer chromatography (silica gel), using as eluent the mixture formed by methylene chloride/ethyl acetate/methanol (70:30:10), presents one single band at Rf=0.61.

EXAMPLE 18

N-trifluoroacetyl Sphingosine 5.0 gr of sphingosine (16.70 mM) prepared according to example 4, are treated with 2.0 gr of trifluoroacetic acid (17.54 mM) and 4.1 gr of dicyclohexylcarbodiimide (20.04 mM) in 150 ml of N,N-dimethylformamide, at 60° C. for 24 hrs.

The solvent is evaporated and the residue gathered in chloroform and kept at −20° C. overnight.

The organic solution is filtered and evaporated under reduced pressure. The residue is purified by preparative chromatography using a silica gel column and eluting the mixture with methylene chloride/ethyl acetate/methanol (70:30:5).

It is evaporated and thrice crystallized from ethyl ether. It is vacuum dried to obtain a solid which melts at 86° C.

Yield 6.2 g.

Thin layer chromatography (silica gel), using as eluent a mixture formed by methylene chloride/ethyl acetate/methanol (70:30:10) presents one single band at Rf=0.7.

EXAMPLE 19

N-pentafluoropropionyl Sphingosine 5.0 gr of sphingosine (16.70 mM), prepared according to Example 4, and 5.7 gr of pentafluoropropionyl anhydride (18.37 mM) are left to react in 150 cc of pyridine, at room temperature for 24 hours. The reaction mixture is concentrated in a rotary evaporator, gathered with chloroform and washed with abundant H$_2$O. The lower phase is anhydrified and the raw material is purified by chromatography, using a mixture of CH$_2$Cl$_2$/ethyl acetate/CH$_3$OH, 70:30:1 v/v/v.

The fraction containing the product is concentrated in a rotary evaporator, and the residue is partitioned by the Folch method. It is crystallized from ethyl ether, thus obtaining a product with a melting point of 98° C.

Yield: 6.8 g.

Thin layer chromatography (silica gel) presents one single band, at Rf approximately 0.67 in CH$_2$Cl$_2$/ethyl acetate/CH$_3$OH (70:30:10 v/v/v).

EXAMPLE 20

N-(N'-acetylglycyl) Sphingosine 5.0 gr of sphingosine (16.70 mM), prepared according to Example 4, 2.1 gr of N-acetylglycine (18.37 mM) and 3.8 gr of dicyclohexylcarbodiimide (18.40 mM) are left to react in 150 cc of chloroform, under warm conditions overnight. The reaction mixture is placed in a freezer to precipitate. The urea is filtered, and the chloroform solution is washed with H$_2$O. The raw material is purified by chromatography using a mixture of CH$_2$Cl$_2$/ethyl acetate/CH$_3$OH, 70:30:10 v/v/v.

The fraction containing the product is concentrated in a rotary evaporator, and the residue is partitioned according to the method of Folch. The resultant is crystallized from ethyl acetate, thus obtaining a product with a melting point of 135° C. (softening at 129° C.).

Yield: 5.2 g.

Thin layer chromatography (silica gel) presents one single band, with Rf approximately 0.16 in CH$_2$Cl$_2$/ethyl acetate/CH$_3$OH (70:30:10 v/v/v).

EXAMPLE 21

B-ethionyl Sphingosine 5.0 gr of sphingosine (16.70 mM), prepared according to Example 4, and 7.6 gr of the p-nitrophenyl ester of N-phthalimide-L-ethionine (18.37 mM) are reacted in 150 cc of ethanol, under warm conditions overnight.

The solvent is evaporated, and the reaction product is gathered in chloroform. It is washed with a solution of 10% NaHCO$_3$ and with H$_2$O. The raw material is purified by chromatography using prep LC 500 A/Waters, eluting with a mixture of CH$_2$Cl$_2$/ethyl acetate/CH$_3$OH 70:30:1 v/v/v.

The product obtained (5.0) is treated with 1 cc of hydrazine hydrate, 80% in 70 cc of ethanol, under warm conditions. It is then cooled and HCl 2N is added until neutrality is reached. The resultant is evaporated, and the raw material is purified by chromatography, eluting with a mixture of CHCl$_3$/CH$_3$OH/NH$_4$OH 30%, (95:5:0.2 v/v/v). The residue is partitioned by the Folch method. The product is crystallized from ethyl acetate, thus obtaining a crystalline solid with a melting point of 92° C.

Yield=2.8 g.

Silica gel chromatography of the product presents one single band with Rf approximately 0.57 in CHCl$_3$/CH$_3$OH/H$_2$O/NH$_4$OH 30%, 80:20:1.7:0.3 v/v/v/v.

EXAMPLE 22

N-(R)-3-hydroxybutyryl Sphingosine 5.0 gr of sphingosine (16.70 mM), prepared according to Example 4, are treated with 1.8 gr of (R)-(–)-3-hydroxybutyric acid (17.54 mM) and 4.1 gr of dicyclohexylcarbodiimide (20.04 mm) in 100 ml of pyridine at room temperature for 24 hours. The solvent is evaporated, and then the residue is gathered in CHCl$_3$ and washed with H$_2$O. The lower phase is anhydrified and the organic solution is evaporated at reduced pressure. The raw material is purified with prep LC 500 A/Waters, using a 100 silica gel column and eluting mixture: CH$_2$Cl$_2$/ethyl acetate/CH$_3$OH, 70:30:3 v/v/v; flow 150 ml/min.

The fraction is evaporated, partitioned according to Folch and crystallized three times from ethyl acetate. It is then vacuum-dry, obtaining a solid with a melting point of 86° C.

Yield=6.0 g.

Silica gel chromatography of the product presents one single band at Rf approximately 0.41 in CH$_2$Cl$_2$/ethyl acetate/CH$_3$OH (70:30:10 v/v/v) and at Rf approximately 0.08 in CHCl$_3$/CH$_3$OH/NH$_4$OH 30% (95:5:0.2 v/v/v).

EXAMPLE 23

N-fluoroacetyl Sphingosine 5.0 gr of sphingosine (16.70) mM), prepared according to Example 4, are reacted with 2.1 gr of the sodium salt of fluoroacetic acid (20.88 mM), in the presence of 5.3 gr of 2-chloro-1-methylpyridine iodide (20.88 mM) and 5.8 cc of triethylamine (42.00 mM) in 80 cc of dimethylformamide, at room temperature overnight. The solvent is evaporated, and the residue is gathered in CH$_2$Cl$_2$ and washed with H$_2$O. It is anhydrified and purified by chromatography, eluting with a mixture of CH$_2$Cl$_2$/ethyl acetate/CH$_3$CH 70:30:1 v/v/v.

The pure fraction is evaporated in a rotary evaporator gathered in CHCl$_3$, and partitioned according to Folch.

The product is crystallized three times from ethyl ether, obtaining a solid with a melting point of 87° C.

Yield=1.2 g.

Silica gel chromatography of the product presents one single band at Rf approximately 0.52 in CH$_2$Cl$_2$/ethyl acetate CH$_3$OH (70:30:10 v/v/v).

EXAMPLE 24

N-(ethyl adipyl) Sphingosine 5.0 gr of sphingosine (16.70 mM), prepared according to Example 4, are reacted with 5.4 gr of the p-nitrophenyl ester of adipic acid monoethyl ester (18.37 mM) in 150 cc of ethanol, under warm conditions overnight. The reaction mixture is evaporated, gathered in chloroform and washed with a solution of 10% NaHCO$_3$, then with H$_2$O. It is purified by chromatography, eluting with a mixture of CH$_2$Cl$_2$/ethyl acetate/CH$_3$OH 70:30:3 v/v/v.

The fraction containing the pure product is partitioned according to the Folch method with saline. It is crystallized three times from ethyl acetate, thus obtaining a product with a melting point of 64° C.

Yield=6.0 g.

Silica gel chromatography of the product presents one single band, with Rf approximately 0.54 in CH$_2$Cl$_2$/ethyl acetate/CH$_3$OH (70:30:10 v/v/v).

EXAMPLE 25

Pharmaceutical Preparations in Solution for Injection

Preparation No. 1—one 2 ml vial contains:

| active substance | mg 50 |
|---|---|
| sodium chloride | mg 16 |
| Citrate buffer pH 6 in | |
| distilled apyrogen water to | ml 2 |

The active substance is chosen from the group formed by the sphingosine derivatives described in Example 6.

Preparation No. 2—one 4 ml vial contains:

| active substance | mg 100 |
|---|---|
| sodium chloride | mg 32 |
| citrate buffer pH 6 in | |
| distilled apyrogen water to | ml 4 |

The active substance is chosen from the group constituted by the sphingosine derivatives described in Example 6.

Preparations Nos. 1 and 2 can be directly administered to animals or humans by any one of the above administration routes. Furthermore, the compounds may contain pharmaceutically active substances.

EXAMPLE 26

Pharmaceutical Compositions Prepared in Double Flacons

The preparations illustrated in this Example are prepared in double flacons. The first flacon contains the active substance in the form of a freeze-dried powder in quantities which may vary between 10% and 90% by weight together with a pharmaceutically acceptable excipient, glycine or mannitol. The second flacon contains the solvent, such as a sodium chloride solution and a citrate buffer.

The contents of the two flacons are mixed immediately before use and the powder of the freeze-dried active substance rapidly dissolves, giving an injectable solution. The pharmaceutical form of a flacon containing the freeze-dried powder of the active substance is the preferred form of the present invention.

System No. 1 a. one 3 ml freeze-dried vial contains:

| active substance | mg 50 |
|---|---|
| glycine | mg 25 | b. one 3 ml vial of solvent contains:

| sodium chloride | mg 24 |
|---|---|
| citrate buffer in distilled water to | ml 3 |

The active substance is chosen from the group formed by the sphingosine derivatives described in Example 6.

System No. 2 a. one 3 ml freeze-dried vial contains:

| active substance | mg 50 |
|---|---|
| mannitol | mg 20 | b. one 3 ml vial of solvent contains:

| sodium chloride | mg 24 |
|---|---|
| citrate buffer in distilled water to | ml 3 |

The active substance is chosen from the group formed by the sphingosine derivatives described in Example 6.

EXAMPLE 27

Pharmaceutical Preparations for Transdermal Administration

Preparation No. 1—one plaster contains:

| active substance | mg 100 |
|---|---|
| glycerin | g 1.6 |
| polyvinyl alcohol | mg 200 |
| Polyvinylpyrrolidone | mg 100 |
| excipient to aid transdermal penetration | mg 20 |
| water | g 1.5 |

The active substance is chosen from the group formed by the sphingosine derivatives described in any one of Examples 7, 9 and 10.

Preparation No. 2—100 gr of ointment contains:

| active substance (in 5g of mixed phospholipid liposomes) | g 4.0 |
|---|---|
| monostearate polyethylene glycol | q 1.5 |
| glycerin | g 1.5 |
| p-oxybenzoic acid ester | mg 125 |
| water | g 72.9 |

The active substance is chosen from the group formed by the sphingosine derivatives described in any one of Examples 8, 11 and 14.

EXAMPLE 28

Pharmaceutical Preparations for Oral Administration

Preparation No. 1—one tablet contains:

| active substance | mg 20 |
|---|---|
| microcrystalline cellulose | mg 150 |
| lactose | mg 20 |
| amide | mg 10 |
| magnesium stearate | mg 5 |

The active substance is chosen from the group formed by the sphingosine derivatives described in Example 15 or 18.

Preparation No. 2—one pill contains:

| | | |
|---|---|---|
| active substance | mg | 30 |
| carboxymethyl cellulose | mg | 150 |
| amide | mg | 15 |
| shellac | mg | 10 |
| saccharose | mg | 35 |
| coloring | mg | 0.5 |

The active substance is chosen from the group formed by the sphingosine derivatives described in Example 12 or 13.

Preparation No. 3—one gelatinous capsule contains:

| | | |
|---|---|---|
| active substance | mg | 40 |
| lactose | mg | 100 |
| gastroresistant coating | mg | 5 |

The active substance is chosen from the group formed by the sphingosine derivatives described in Example 12 or 13.

Preparation No. 4—one soft gelatin capsule contains:

| | | |
|---|---|---|
| active substance | mg | 50 |
| vegetable oil | mg | 200 |
| beeswax | mg | 20 |
| gelatin | mg | 150 |
| glycerin | mg | 50 |
| coloring | mg | 3 |

The active substance is chosen from the group formed by the sphingosine derivatives described in Example 12 or 13.

The following is claimed:

1. N-acyllysosphingolipids of one of the two formulae

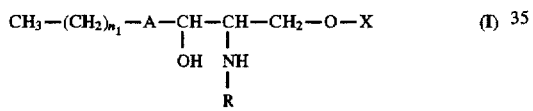

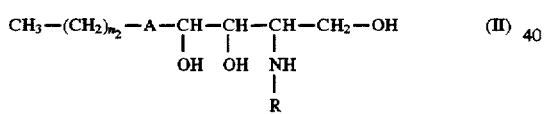

in which -A represents the group —CH=CH— or —CH$_2$—CH$_2$—, n$_1$ is a whole number between 6 and 18, n$_2$ is a whole number between 11 and 15, X is a hydrogen atom a monosaccharide, a disaccharide or phosphorylcholine and R represents an acyl radical derived from an aliphatic acid having from 2 to 24 carbon atoms, substituted by one or more polar groups selected from the group consisting of:

chlorine, bromine and fluorine;

hydroxy groups esterified with an organic or inorganic acid;

etherified hydroxy groups;

keto, ketal, and acetal groups derived from lower aliphatic or araliphatic alcohols;

ketoxime, aldoxime or hydrazone groups optionally substituted by lower alkyl or aralkyl groups;

free mercapto groups or mercapto groups esterified with a lower aliphatic or araliphatic acid or etherified with lower aliphatic or araliphatic alcohols;

free or esterified carboxy groups;

free sulfonic groups or sulfonic groups esterified with lower aliphatic or araliphatic alcohols;

sulfamide groups or sulfamide groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups;

and derivatives thereof with peracylated hydroxy groups, with the exception of N-(γ-amino-butyryl) sphingosine, N-(dichloroacetyl)sphingosine and N-(dichloroacetyl) dihydrosphingosine, or mixtures of said N-acyllysosphingolipids, and metal or organic base salts or acid addition salts thereof.

2. N-acylphytosphingosines in which the acyl group is derived from an acid as defined in claim 1.

3. A process for the preparation of N-acyllysosphingolipids and of their derivatives as defined in claim 1, which comprises acylating, optionally after temporarily protecting the functional groups in the acylating component, a lysosphingolipid of one of the formulae I or II in which in place of R a hydrogen atom is present, or mixtures of these compounds, with an aliphatic acid having from 2 to 24 carbon atoms, substituted by one or more polar groups selected from the group consisting of:

chlorine, bromine and fluorine;

hydroxy groups esterified with an organic or inorganic acid;

etherified hydroxy groups;

keto, ketal, and acetal groups derived from lower aliphatic or araliphatic alcohols;

ketoxime, aldoxime or hydrazone groups optionally substituted by lower alkyl or aralkyl groups;

free mercapto groups or mercapto groups esterified with a lower aliphatic or araliphatic acid or etherified with lower aliphatic or araliphatic alcohols;

free or esterified carboxy groups;

free sulfonic groups or sulfonic groups esterified with lower aliphatic or araliphatic alcohols;

sulfamide groups or sulfamide groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups;

and, if desired, the polar groups substituted on the acyl group can be converted one into the other, and, if desired, the products obtained can be converted into their salts.

4. A process according to claim 3, in which the starting material is reacted with a reactive functional derivative of the acid.

5. A process according to claim 3, comprising a method chosen from the following group of reactions:

1. reaction of the lysosphingolipid derivative with the acid azide;

2. reaction of the lysosphingolipid derivative with an acylimidazole;

3. reaction of the lysosphingolipid derivative with a mixed anhydride of the acid and of trifluoroacetic acid;

4. reaction of the lysosphingolipid derivative with the chloride of the acid;

5. reaction of the lysosphingolipid derivative with the acid in the presence of a carbodiimide and optionally in the presence of 1-hydroxybenzotriazol;

6. reaction of the lysosphingolipid derivative with the acid at a high temperature;
7. reaction of the lysosphingolipid derivative with a methyl ester of the acid at a high temperature;
8. reaction of the lysosphingolipid derivative with a phenol ester of the acid; or
9. reaction of the lysosphingolipid derivative with an ester derived from the exchange between a salt of the acid and 1-methyl-2-chloropyridine iodide or analogous products thereof.

6. A process according to claim 3 or 5, in which free primary or secondary amino groups or carboxy groups are temporarily protected during the acylation reaction on the hydroxy groups.

7. A process according to claim 3 or 5, in which the procedure is interrupted at any one stage or in which it is started at an intermediate stage and the remaining stages are then carried out.

8. An N-acyllysosphingolipid of the formula

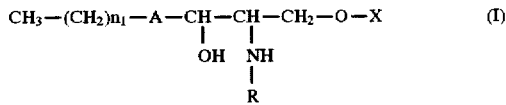

$$CH_3-(CH_2)_{n_1}-A-CH-CH-CH_2-O-X \quad (I)$$
$$\phantom{CH_3-(CH_2)_{n_1}-A-}\underset{OH}{|}\phantom{-}\underset{\underset{R}{NH}}{|}$$

in which -A represents the group —CH=CH— or —CH$_2$—CH$_2$—, $n_1$ is a whole number between 6 and 18, X is a hydrogen atom or a disaccharide or phosphorylcholine and R represents an acyl radical derived from an aliphatic acid having from 2 to 24 carbon atoms, substituted by one or more polar groups selected from the group consisting of hydroxy groups esterified with an organic or inorganic acid;
etherified hydroxy groups;
keto, ketal, and acetal groups derived from lower aliphatic or araliphatic alcohols;
ketoxime, aldoxime or hydrazone groups optionally substituted by lower alkyl or aralkyl groups;
free mercapto groups or mercapto groups esterified with a lower aliphatic or araliphatic acid or etherified with lower aliphatic or araliphatic alcohols;
free or esterified carboxy groups;
free sulfonic groups or sulfonic groups esterified with lower aliphatic or araliphatic alcohols;
sulfamide groups or sulfamide groups substituted by lower alkyl or aralkyl groups or lower alkylene groups;
sulfoxide or sulfone groups derived from lower alkyl or aralkyl groups;
nitrile groups;
free or substituted amino groups, and quaternary ammonium derivatives of such amino groups;
or derivatives thereof with peracylated hydroxy groups, with the exception of N-(dichloroacetyl)sphingosine and N-(dichloroacetyl) dihydrosphingosine,
or mixtures of said N-acyllysosphingolipids, or a metal or organic base salt or acid addition salt thereof.

9. An N-acyllysosphingolipid according to claim 8, in which the acyl group is derived from an acid with a straight chain having a maximum of 12 carbon atoms.

10. N-acyllysosphingolipids according to claim 8, in which the acyl group is derived from an acid with a branched chain, in which the lateral chains are alkyls with a maximum of 4 carbon atoms and the acid has a maximum of 12 carbon atoms.

11. N-acyllysosphingolipids according to claim 8, in which from 1 to 3 polar groups are substituted on the acyl radical.

12. Peracylated derivatives of N-acyllysosphingolipids according to claim 8, derived from aliphatic acids having a maximum of 6 carbon atoms.

13. Peracylated derivatives of N-acyllysosphingo-lipids according to claim 12, wherein the aliphatic acids are derived from formic, acetic, propionic, butyric, valeric or caproic.

14. Peracylated derivatives of N-acyllysosphingolipids according to claim 12, derived from hydroxy acids, aminoacids or dibasic acids.

15. Peracylated derivatives of N-acyllysosphingolipids according to claim 12, derived from aromatic acids having a single benzene nucleus, optionally substituted by hydroxy, amino or carboxy groups.

16. N-acyllysosphingolipids according to claim 8, in which X represents a disaccharide selected from the group consisting of saccharose, lactose, cellobiose and maltose.

17. N-acyllysosphingolipids according to claim 15 or 16, having as the base mixtures of lysosphingolipids obtainable by deacylation of natural sphingolipids.

18. N-acyllysosphingolipids according to claim 8, having as the base lysosphingolipid one selected from the group consisting of sphingosine, dihydrosphingosine, psychosine, dihydropsychosine, phosphorylcholine-sphingosine and phosphorylcholine-dihydrosphingosine.

19. N-acyldihydrosphingosines in which the acyl group is derived from an acid as defined in claim 8.

20. N-acylpsychosine in which the acyl group is derived from an acid as defined in claim 8.

21. N-acyl dihydropsychosine in which the acyl group is derived from an acid as defined in claim 8.

22. N-acyl phosphorylcholinesphingosine in which the acyl group is derived from an acid as defined in claim 8.

23. N-acyl phosphorylcholinedihydrosphingosine in which the acyl group is derived from an acid as defined in claim 8.

24. The N-acyllysosphingolipid according to claim 8 having as the base lysosphingolipid sphingosine and as the acyl group the maleyl group, and metal or organic base salts thereof.

25. A pharmaceutical composition comprising a pharmaceutically effective amount of a compound according to claim 8 as the active ingredient and a pharmaceutically acceptable excipient.

26. A pharmaceutical composition according to claim 25, in which the active ingredient is one or more of the compounds selected from the group consisting of compounds of the formula I in which the disaccharide is saccharose, lactose, cellobiose or maltose, and the lysosphingolipid portion of the compound is selected from the group consisting of sphingosine, dihydrosphingosine, psychosine, dihydropsychosine, phosphorylcholine-sphingosine and phosphorylcholine-dihydrosphingosine.

27. A pharmaceutical composition according to claim 25, in which the active ingredient is N-maleylsphingosine.

28. An N-acyllysosphingolipid of the formula

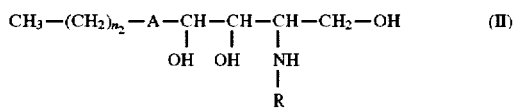 (II)

in which -A represents the group —CH=CH— or —CH$_2$—CH$_2$—, n$_2$ is a whole number between 11 and 15, and R represents an acyl radical derived from an aliphatic acid having from 2 to 24 carbon atoms, substituted by one or more polar groups with the exception of chlorine, bromine and fluorine;

or derivatives thereof with peracylated hydroxy groups, or mixtures of said N-acyllysosphingolipids, or a metal or an organic base salt or an acid addition salt thereof.

29. A pharmaceutical composition comprising a pharmaceutically effective amount of a compound according to claim 28 as the active ingredient and a pharmaceutically acceptable excipient.